United States Patent [19]

Nelson et al.

[11] Patent Number: 4,725,388
[45] Date of Patent: Feb. 16, 1988

[54] NON-FLUORESCENT VESSELS FOR HOLDING TEST SAMPLES IN FLUORESCENT ASSAYS

[75] Inventors: Keith E. Nelson, Verdes, Calif.; Claude C. Crawford, Annapolis, Md.

[73] Assignee: Dynatech Laboratories, Inc., Chantilly, Va.

[21] Appl. No.: 11,510

[22] Filed: Feb. 6, 1987

Related U.S. Application Data

[60] Division of Ser. No. 735,107, May 17, 1985, abandoned, which is a continuation of Ser. No. 433,826, Oct. 12, 1982, abandoned.

[51] Int. Cl.⁴ .............................................. C09K 11/00
[52] U.S. Cl. ....................................... 264/21; 264/349
[58] Field of Search ....................... 264/21, 349; 435/4, 435/30, 7; 422/56, 57, 68, 61; 450/458.1, 461.1, 461.2, 462.1, 463.1

[56] References Cited

U.S. PATENT DOCUMENTS

| | | | |
|---|---|---|---|
| 4,100,416 | 7/1978 | Hirschfeld | 250/461.1 |
| 4,272,505 | 6/1981 | Smith | 435/7 |
| 4,582,809 | 4/1986 | Block et al. | 422/68 |
| 4,622,291 | 11/1986 | Picciolo et al. | 435/4 |

*Primary Examiner*—Frank Sever
*Attorney, Agent, or Firm*—Lowe, Price, LeBlanc, Becker & Shur

[57] ABSTRACT

A vessel for holding at least one test sample to be measured for its fluorescence, wherein the vessel is formed from a material having a native fluorescence, and wherein the vessel is provided with a barrier which blocks penetration or at least reduces the extent of penetration of an exciting light into the vessel's fluorescable material to prevent fluorescent excitation of the vessel or at least reduces the extent to which the vessel is fluorescently excited when exposed to an exciting light during the fluorometric measurement.

5 Claims, 11 Drawing Figures

BLACK PIGMENT COATING

WHITE PIGMENT COATING

NON-FLUORESCENT VESSELS FOR HOLDING TEST SAMPLES IN FLUORESCENT ASSAYS

This application is a division of application Ser. No. 735,107, filed May 17, 1985, abandoned, which is a continuation of application Ser. No. 433,826, abandoned filed Oct. 12, 1982.

FIELD OF THE INVENTION

This invention generally relates to laboratory equipment for use in conducting fluorescent assays and is particularly concerned with vessels for holding test samples to be measured for their fluorescence.

BACKGROUND

Fluorescent assays are now commonly used for diagnostic and research purposes to detect and measure the quantity of a wide variety of immunological and non-immunological substances. In fluorescent immunoassays, the test sample may be prepared for fluorometric measurement in a variety of different ways.

For example, a fluorescently labeled reactant may be immunologically reacted with the immunological substance of interest which is usually directly or indirectly immobilized on a solid phase. Following separation of the nonspecific substances which are not attached to the substance of interest, the fluorescence of the reaction product is measured to determine the amount of the substance of interest. In another type of fluorescent immunoassay, an enzyme labeled reactant is attached to the immunological substance of interest, and a fluorogenic substrate is catalyzed by the enzyme label to yield a fluorescent product which can be fluorescently measured to determine the quantity of the substance of interest.

In carrying out fluorescent assays of the foregoing type and also other types, microtest plates (or microtitration plates, as they are also called) and strips of microtest wells are often used. Microtest plates are formed with a multiplicity of wells which are joined together in a molded one-piece structure for containing microliter quantities of fluid samples. Examples of a microtest plate and microtest wells in strip form are described in U.S. Pat. No. 4,154,795 which issued to A. C. Thorne on May 15, 1979.

The use of microtest plates and microtest strips of wells in fluorescent and other types of assays offers several important advantages. First, they permit the mass preparation of a large number of test sample solutions at the same time. Second, they are more convenient to handle as compared with individual test tubes. Third, they can easily and inexpensively be washed. Fourth, they are inexpensive and disposable. Fifth, they are customarily formed from plastic materials which are not fragile like glass. Sixth, they can be made from a material having an ability to attract certain molecules such as protein molecules so that they can serve as a solid phase in an immunoassay. Polystyrene and polyvinyl chloride are commonly used for this purpose and exhibit acceptable protein binding properties for attracting protein molecules.

The use of plastic materials permits the microtest plates and strips to be manufactured by low cost, mass production molding techniques.

For fluorescent assays, however, molded microtest plates and strips of the type described above have a serious drawback in that the moldable materials customarily used for low cost manufacture exhibit a substantial level of native fluorescence, particularly at the exciting light wave lengths commonly employed in fluorometers. When used to hold a test sample in a fluorometer for making a fluorometric measurement they therefore will unavoidably be excited along with the test sample by the fluorometer's exciting light. As a result, the microtest plates, strips or their individual wells will fluoresce to produce spurious light emissions which interfere with and impair an accurate measurement of the intensity of the light emitted from the excited test sample itself. These spurious light emissions have the objectionable effect of creating a noise signal in the fluorometer's detector to significantly reduce the signal-to-noise ratio.

One solution to the foregoing problem is to equip the fluorometers with special, sample-holding vessels made of non-fluorescent or low-fluorescing materials such as quartz or certain kinds of glass. In addition, optical grade Teflon has been suggested as a non-fluorescing material for making fluorometer flow cells in U.S. Pat. No. 4,008,397 which issued to J. J. Zdrodowski on Feb. 15, 1977. Also, an Italian company called Kartell is marketing a molded cuvette of undisclosed plastic material which is claimed to have a sufficiently low level of fluorescence to make it suitable for holding samples in a fluorometer. Although the level of fluorescence of the Kartell cuvette is lower than that of clear polystyrene, it nevertheless is significant.

The foregoing cuvettes and test tubes share a common drawback in that they are each capable of holding only a single test sample. Vessels of this type are therefore less convenient to work with as compared with microtest plates or strips. More particularly, they are not suitable for the mass preparation of test samples as with microtest plates and strips. In addition, they are more difficult and more expensive to wash in the course of performing the various steps in an immunoassay.

Furthermore, quartz and glass are not suitable for making the intricately shaped microtest plates and strips because the manufacturing costs would be prohibitively high. In addition, the protein binding properties of quartz and glass are inferior to the protein binding properties of polystyrene and other plastics which are customarily used for making microtest plates and strips. They therefore are not as suitable as polystyrene and other plastics for defining a solid phase in an immunoassay. Finally, they are fragile and are not intended to be disposable.

Because of the disadvantages associated with cuvettes or tubes, it is often desirable and sometimes necessary to prepare the test samples in a standard microtest plate or strip and then to transfer the samples to the cuvettes or tubes for measurement. Transferring the test samples is time consuming, inconvenient and increases the cost of the fluoroescent assay.

From the foregoing, it is clear that, on the one hand, there are easily moldable materials (such as polystyrene and polyvinyl chloride) which are suitable for use in low cost, mass production of microtest plates and other sample-holding vessels, but which exhibit a substantial level of native fluorescence to create a problem in measuring the fluorescence of test samples. On the other hand, there are materials such as quartz and certain kinds of glass which have low levels of native fluorescence to avoid the foregoing problem, but which are unsuitable for the low cost production of microtest plates and strips.

SUMMARY AND OBJECTS OF INVENTION

With the foregoing in mind, the general aim and purpose of this invention is to provide a novel, low cost, sample-holding vessel in which the native fluorescence of the material used to form the vessel is effectively suppressed or reduced to enhance the fluorometer's signal-to-noise ratio in a fluorometric measurement.

By suppressing the vessel's native fluorescence, virtually any desired material may be used for forming the vessel, including those which are used to make present day microtest plates and strips. With this invention, microtest plates and strips may therefore be manufactured with their customary materials (such as polystyrene or polyvinyl chloride) at low, affordable costs without encountering the problem associated with the material's native fluorescence. Vessels made in accordance with this invention are therefore suitable both for preparing the test sample and for holding the prepared test sample during the fluorometric measurement.

The foregoing object is achieved by providing the vessel with a barrier which blocks any significant penetration of the fluorometer's exciting light into the body of the sample-holding vessel, thereby preventing the vessel's material from being excited during the fluorometric measurement. When exposed to the fluorometer's exciting light, therefore, the vessel itself will not emit any significant light to interfere with the fluorometric measurement of the light emissions from the excited test sample. The signal-to-noise ratio in the fluorometer's detector is therefore improved to improve the accuracy of the fluorometric measurement.

In the illustrated embodiment, the barrier is of the physical type which is non-chemically incorporated with the vessel's material and which therefore does not alter the chemical properties of the vessel's material. The barrier may be formed by dispersing a particulate, barrier-defining material throughout the body of the vessel or by coating a preformed vessel with a barrier-defining material.

In the illustrated embodiments, the material used to form the barrier is a pigment which is opaque or substantially opaque to the wave length of the fluorometer's exciting light source and which is non-fluorescent or at least exhibits low fluorescence at the wave length of the light emitted from the excited test sample.

Black pigment is especially suitable for forming the barrier in the sample-holding vessel of this invention. It is opaque to and absorbs all light wave lengths. A plastic vessel containing a black pigment barrier exhibits virtually no detectable light emission when subjected to light in the ultraviolet range.

White pigment is also highly suitable for forming the barrier in the sample-holding vessel of this invention. While a vessel containing a white pigment barrier will fluorescent to some extent when exposed to ultraviolet light, the white pigment has the effect of appreciably strengthening the light emission produced by exciting the test sample, thereby improving the signal-to-noise ratio by both strengthening the signal of interest (the wave length of the light emitted by the excited test sample) and reducing the objectionable noise signal (the spurious light emission from the vessel itself).

Apart from white and black pigments, pigments of certain colors may also be suitable as long as they are opaque to the wave lengths of the fluorometer's exciting light and are non-fluorescent or exhibit low fluorescence at the wave length of the light emitted by the excited test sample.

Instead of using a pigment coating, a suitable metal such as silver may be deposited on appropriate surfaces of a preformed vessel to form the barrier that is opaque to the fluorometer's exciting light.

It will be appreciated that the vessel incorporating the principles of this invention is advantageously molded by low cost mass production techniques. Furthermore, the vessel incorporating the principles of this invention may be of any desired type such as a microtest plate, a microtest strip of wells, individual wells themselves, cuvettes and test tubes.

Further objects of this invention will appear as the description proceeds in connection with the appended claims and the below-described drawings.

DETAILED DESCRIPTION

For convenience, the term "vessel" is used in this specification (including the claims) to mean microtest plates, strips of wells, individual wells, cuvettes, test tubes or any other receptacle for holding a liquid. Also, the term "light" as used in this specification refers to both non-visible light (e.g., ultraviolet light) and light which is visible to the naked eye.

Figure 1:
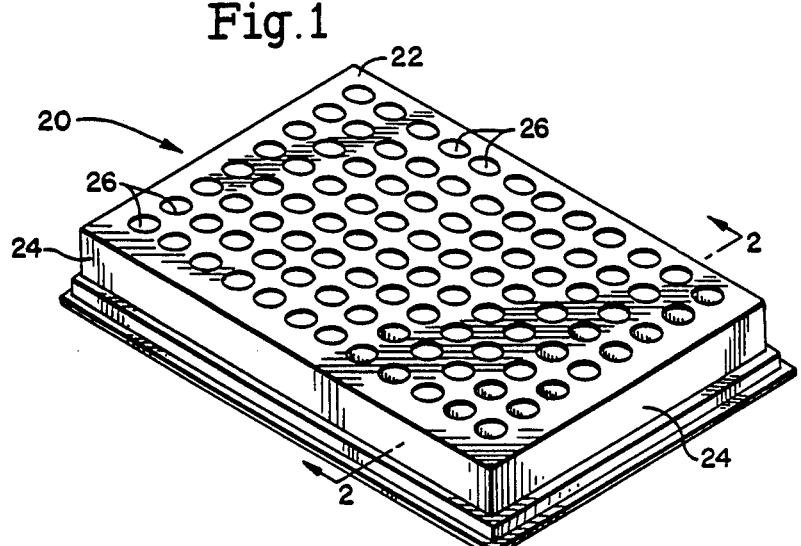
FIG. 1 is a perspective view of a 96 well microtest plate incorporating the principles of this invention.
Figure 2:
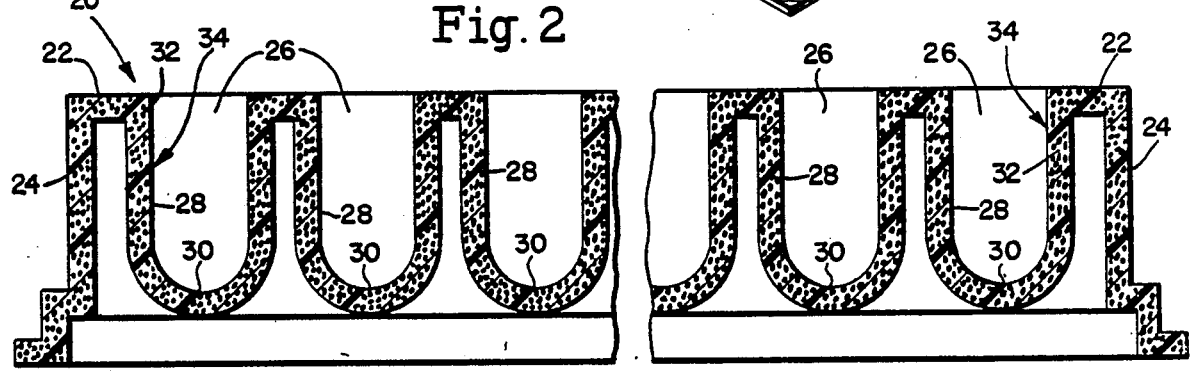
FIG. 2 is an enlarged, fragmentary section taken substantially along lines 2—2 of FIG. 1.

Referring to FIGS. 1 and 2, a molded, one-piece, rectangular microtest plate 20 incorporating the principles of this invention is integrally formed with a flat top wall 22 and side walls 24 depending from top wall 22 to form a depending skirt along all four sides of the plate to support the plate on a flat horizontal surface. Plate 20 is additionally formed with a multiplicity of precisely dimensioned, upwardly opening wells (or cups as they are also called) 26 for holding micro-liter quantities of liquid test samples or other solutions.

Figure 4:
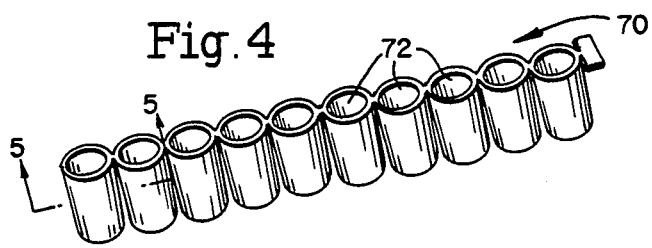
FIG. 4 is a perspective view of a microtest strip of wells.

Wells 26 are integral with and open at top wall 22. By this construction, wells 26 are integrally joined to each other through top wall 22 and, unlike the embodiment shown in FIG. 4, are not intended to be separated from each other.

As best shown in FIG. 2, wells 26 depend from top wall 22 to lie in the region delimited by side walls 24. Wells 26 are uniformly spaced apart from each other and are uniformly dimensioned. Each of the wells 26 is formed with a cylindrical side wall 28 and a suitable bottom 30. The thicknesses of the wells' side and bottom walls are essentially uniform and are relatively small. The longitudinal axes of wells 26 are parallel and normally intersect top wall 22. In the embodiment illustrated in FIGS. 1 and 2, there are twelve parallel spaced apart rows of wells with eight wells in each row to provide the standard total of 96 wells.

The foregoing type of microtest plate is essentially the same as the one described in U.S. Pat. No. 3,356,462 which issued to N. M. Cooke et al on Dec. 5, 1967. The disclosure in U.S. Pat. No. 3,356,462 is incorporated into this specification by reference.

Plate 20 is preferably formed from commercially available polystyrene or polyvinyl chloride for use in immunoassays. For example, the polystyrene may be any one of the following: Gulf SMD 3500, Foster Grant 9100D, Monsanto Lustrex 777 or Dow Chemical clear general purpose 666U. Plate 20 may alternatively be formed from any one of a number of other moldable materials such as acrylonitrile—butadiene—styrene and related multipolymers, acetal and homopolymer and copolymers thereof (Delrin for example), acrylics such as Plexiglass, allyl esters, amino resins, cellulosic plastics, epoxies, certain fluoroplastics, furan resin, ionomers, nitrile resins, phenolics, modified phenylene oxide, polyamide (nylon), polyamide—imide, polybutylene, polycarbonate (Lexan for example), polyester derivatives, polyethylene and ethylene copolymers, ethylene—vinyl acetate, polyimide, polymethylpentene, polyphenylene sulfide, polypropylene, derivatives of polystyrene, polyurethane, vinyl and polyvinyl copolymers other than polyvinyl chloride, silicone, styrene—acrylonitrile, sulfone polymers, vinylidene chloride and polymers and copolymers thereof, and alloys of the above.

The plastic material selected for plate 20 is required to be chemically compatible with the assay substances to be used so as not to upset or interfere with the reactions which take place in assays, particularly immunoassays. In general, the particular application (e.g., immunoassays) determines the material to be used for making plate 20.

In accordance with this invention, pigment particles 32 are uniformly distributed or dispersed throughout plate 20 in sufficient quantity or density to form a barrier 34 which blocks any significant penetration of a fluorometer's exciting light or irradiation into plate 20, thereby preventing any significant excitation of the plate's plastic material during a fluorometric measurement. The pigment-defining barrier therefore has the effect of suppressing the native fluorescence of the plate's plastic material.

It will be appreciated that only the layer of pigment 32 lying immediately adjacent to the exposed surfaces of plate 20 defines the barrier for blocking penetration of the fluorometer's exciting light into plate 20. At best, therefore, only the plastic molecules lying on the plate's exposed surfaces will be fluoresced when exposed to a fluorometer's exciting light. The number of plastic molecules which will be fluoresced will consequently be reduced to a negligible number.

Pigment particles 32 are required to be opaque or at least substantially opaque at least to the wave length range of the fluorometer's exciting light. In addition, pigment particles 32 are require to be non-fluorescent or at least exhibit low fluorescence (which is less than that of the plastic material used to form plate 20) at the wave length of the light emissions resulting from excitation or irradiation of the test samples in wells 26.

Black and white pigments are especially suitable for defining the desired barrier previously mentioned. Other colored pigments such as green and red may also be used for defining barrier 34 for blocking penetration of the fluorometer's exciting light, so long as they are opaque at least to the wave length range of the fluorometer's exciting light and are non-fluorescent or at least exhibit low fluorescence at the wave lengths of the light emissions which result from exictation of the test samples.

A colored pigment other than white will reflect the particular wave length of its color so that the selection of a colored pigment other than white will afford selective enhancement of certain light wave lengths. For example, a red pigment will reflect the red wave length while abosorbing all other wave lengths in the light spectrum.

Black pigment, of course, absorbs all wave lengths in the visible and non-visible light spectrum and will therefore reflect none, while white pigment reflects all wave lengths in the spectrum, while absorbing none. It will be appreciated that the reflection of light produced by white pigment or other colored pigments differs from, and therefore should be distinguished from, light emissions originating from the native fluorescene of the material due to irradiation or excitation by an exciting light or radiation, which is usually in the ultraviolet range.

The pigment selected for establishing barrier 34 in plate 20 is required to be chemically compatible with the substances to be placed in wells 26 so that it does not alter the substances themselves or upset the reactions in assays which are carried out using plate 20. It will be appreciated that pigment particles 32 are merely mixed with the plastic material of plate 20 and therefore are not chemically combined with the plate's plastic material. Pigment particles 32 therefore do not alter the chemical properties of the plate's plastic material.

In order to form barrier 34, it is not necessary that pigment particles 32 be uniformly dispersed throughout plate 20. Instead, they need only be dispersed to an adequate extent to form the desired barrier for blocking penetration of a fluorometer's exciting light into the plate.

From the foregoing description it is evident that the amount of pigment particles 32 incorporated into plate 20 must be sufficient to provent any significant penetration of a fluorometer's exciting light into the microtest plate to thereby suppress or at least reduce the native fluorescene of the plastic material used to form plate 20. On the other hand, the amount of pigment particles 32 used to form barrier 34 should not be so great as to compromise or impair the structural strength of plate 20 or to upset or adversely affect the molding conditions for molding plate 20 from a selected plastic.

In carrying out an embodiment of this invention, pigment particles 32 are added to and thoroughly mixed with the plastic material prior to molding of the plate, so that barrier 34 is effectively formed in situ in the course of molding plate 20 into its final form. A satisfactory barrier may be achieved by adding pigment to the selected plastic material in an amount ranging from about 0.01% to about 10% based on the total weight of the plate's materials (i.e., the weight of the plastic material plus the weight of the pigment particles). Percentages of approximately 0.1% to approximately 1.0%, however, are preferred. The minimum amount of pigment particles will vary depending upon the type of pigment selected and also on the particular applications which plate 20 will be used for. The limit on the maximum amount of pigment will, as previously noted, depend primarily on the desired structural strength of plate 20 or, for that matter, any other vessel which is formed with the pigment-defining barrier of this invention.

In one preparation for the microtest plate for use in fluorescent immunoassays, commercially available carbon based black pigment (PMS 4500 SUDC, which is pure carbon and which is supplied by Plastic Molding Supply, a company located in Brunswick, N.J.) was mixed with commercially available clear polystyrene in an amount equal or proportional to 0.22 pounds (100 grams) of the black carbon pigment per 100 pounds of clear polystyrene. The amount of pigment present in the mixture therefore amounted to slightly less than 0.22% of the total weight of the mixture or exactly 0.22% of the weight of the total weight of the polystyrene. Following mixing to uniformly disperse or distribute the pigment throughout the plastic, microtest plates of the type shown in FIG. 1 were injection molded from the pigment-plastic mixture. Microtest plates produced from this mixture were observed to have a black, opaque appearance.

When exposed to an existing light in the ultraviolet range, plates made from the foregoing black pigment-polystyrene formulation exhibited no detectable light emissions or, at best, only negligible light emissions when exposed to an exciting light in the ultraviolet range. Accordingly, the black-pigmented microtest plates described in the foregoing example have the effect of dramatically increasing the signal-to-noise ratio of a fluorometer's light intensity detector.

In another example, commercially available white pigment (Plastic Molding Supply's PMS 350 SUDC) was mixed with the same polystyrene used in the preceding example in the amounts specified in the first example for black pigment (i.e., 0.22 lbs. of white pigment per 100 lbs. of polystyrene). Microtest plates injection molded from the white-pigmented mixture were found to reduce the intensity of the vessel's fluorescently produced light emissions to almost one-half the value measured for conventional clear polystyrene microtest plates without the pigment-defining barrier of this invention.

Although not reducing the light emissions due to native fluorescence as much as black pigment, the white pigment was found to have the advantageous effect of substantially increasing the intensity of the light emissions resulting from the fluorescent excitation of test samples in the plate's wells, thereby strengthening the signal of interest due to the light emitted by the excited test samples. Accordingly, white pigment has the effect of improving the signal-to-noise ratio in two ways, one by strengthening the signal of interest, and the other by reducing the noise signal due to the plate's native fluorescence. The increase in the intensity of the light emitted by the fluorescently excited test sample in the white-pigmented microtest plate is believed to be due to the high reflection property of white pigment which causes the fluorometer's exciting light and also the emitted light (due to the fluorescent excitation of the test sample) to be reflected from the surfaces of the sample-receiving wells 26 in the microtest plate. This reflection appears to cause the exciting light and the emitted light to move or bounce back and forth through the sample to increase the intensity of the light emitted by the fluorescently excited sample.

Another white pigment considered to be suitable for forming barrier 34 is Dupont's Ti-Pure R-101 CFKD, which is titanium dioxide. It is evident that any other type of white or black pigment may be used so long as it is opaque or at least substantially opaque to the wave length of the fluorometer's exciting light and is non-fluorescent or at least exhibits low fluorescence at the wave length of the light emitted by the fluorescently excited test sample.

Figure 3:
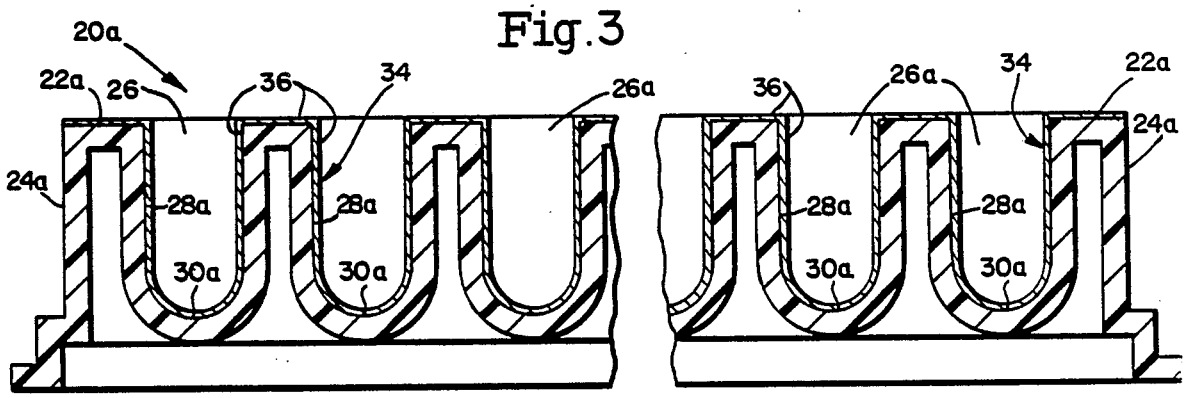
FIG. 3 is an enlarged fragmentary section similar to FIG. 2, but illustrating another embodiment of this invention.

Instead of dispersing the barrier-defining pigment particles 32 into the plate's plastic body, barrier 34 may be established by applying a thin coating or layer of a pigment-containing coloring agent 36 to the exposed surfaces of a preformed microtest plate 20a and especially to those surface areas which will be exposed to the fluorometer's exciting light as shown in FIG. 3.

Plate 20a has the same configuration as plate 20 and is of the same construction as plate 20 except that coating 36 is applied in lieu of dispersing the pigment particles throughout the plastic body of the plate in the manner shown in FIG. 2. The body of the plate 20a is therefore devoid of pigment particles and is formed entirely from a suitable plastic material such as polystyrene or polyvinyl chloride. To the extent that plates 20 and 20a are the same, like reference numerals have been applied to designate like parts, except that the reference numerals used for plate 20a have been suffixed by the letter "a" to distinguish them from those used for plate 20.

The coloring agent used for coating 36 has three major ingredients, namely the pigment, a vehicle for the pigment, and a solvent. When the coloring agent is applied to form coating 36 it is clear that the solvent flashes off as the coating drys, leaving only the pigment and its vehicle. Any suitable vehicle may be used such as polystyrene resin. Any suitable solvent may be used such as methylene chloride. Finally, any suitable pigment may be used so long as it is opaque or at least substantially opaque at least to the wave length of the fluorometer's exciting light and is non-fluorescent or at least exhibits low fluorescence (significantly less than that of the plastic material used to mold plate 20a) at least at the wave length of the fluorescently excited test sample. For example, a black pigment or a white pigment may be used as described above in the preceding examples. Alternatively, a colored pigment may be used, such as red, so long as it is opaque to the wave length of the fluorometer's exciting light and is non-fluorescent or at least exhibits low fluorescence at least at the wave length of the light emission resulting from the fluorescent excitation of the test samples.

The coloring agent selected for forming coating 36 is required to be chemically compatible with the substances placed in wells 26a so that it does not alter the substances themselves or upset the reactions in assays which are carried out in plate 20a. The coloring agent may be applied to plate 20a by spraying or any other suitable means.

In the embodiment shown in FIG. 3, it will be appreciated that plate 20a is first molded or otherwise formed from a suitable plastic. Thereafter, the coloring agent is applied to the appropriate surfaces of the plate to form the barrier-defining coating 36 which prevents penetration of the fluorometer's exciting light into the plate's plastic body.

In the embodiment of FIG. 3, coating 36 is shown to cover the entire top surface of top wall 22 and all of the interior surfaces of wells 26. The barrier formed by coating 36 therefore prevents penetration of a fluorometer's exciting light beam into the plastic body of plate 20a to thereby prevent plate 20a from being fluorescently excited by the exciting light. The exciting light in this embodiment and the embodiment of FIGS. 1 and 2 is directed through the open end of each of the plate's wells. To conduct a fluorometric measurement it therefore will be appreciated that a fluorometer of the frontal approach type is required such as the one schematically shown in FIG. 7.

Figure 7:
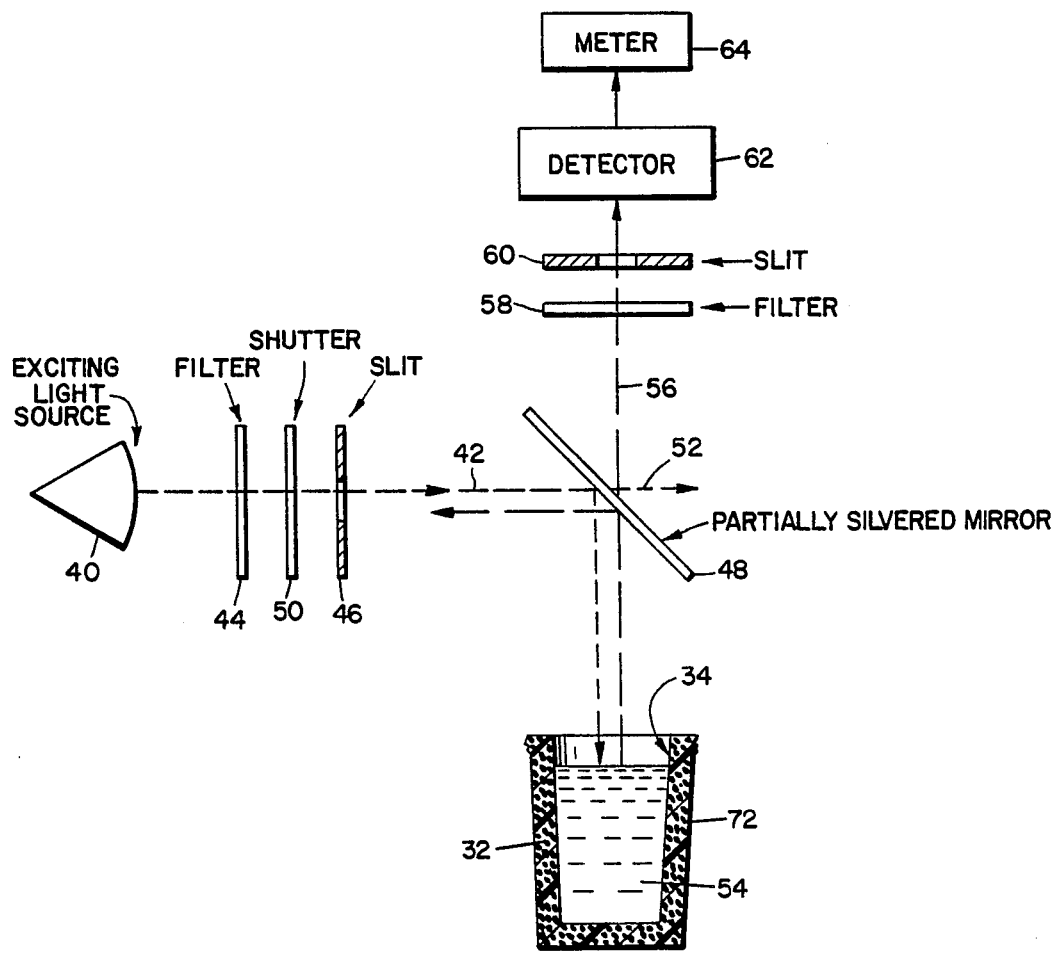
FIG. 7 is a schematic view of a fluorometer which is adapted for use with the sample-holding vessels of this invention.

In FIG. 7, the fluorometer comprises a suitable light source if source of radiation 40 for supplying an exciting light or radiation which may vary from about 200 nanometers to about 700 nanometers depending upon the material to be fluorescent and which is usually in the ultraviolet wave length range.

The exciting light beam developed by source 40 is indicated by arrow 42 and is directed through a filter 44 and a slit or aperture 46 to a partially silvered mirror 48. Mirror 48 is located at an acute angle to the direction of the exciting light from source 40 to reflect the exciting light beam downwardly through the open upper end of a sample holding vessel so that it impinges directly on and penetrates the test sample in the vessel before impinging any of the vessel's surfaces. A shutter 50 may optionally be located between filter 44 and slit 48. The beam of exciting light 42 may be focused or suitably targeted so that upon being reflected by mirror 48 it will enter the vessel through the vessel's open upper end. Because mirror 48 is only partially silvered, part of the exciting light will pass through the mirror and will therefore be wasted as indicated by the arrow 52.

Upon being exposed to the exciting light, the test sample (indicated at 54 in FIG. 7) will be fluorescently excited to emit light at a predetermined wave length or range of wave lengths. The wave length of the emitted light depends on the particular substance which is fluorescently excited and is typically in the range extending from about 350 mm to about 900 mm. The emitted light produced by the excitation of test sample 54 will pass directly upwardly through the open upper end of the vessel and will pass through the partially silvered mirror 48 as indicated by arrow 56. Part of the emitted light will be reflected by the partially silvered mirror and will therefore be wasted.

The emitted light 56 passing through mirror 48 will pass through a further filter 58 (which may be of the bandpass type to pass just the wave length of interest) and another slit or aperture 60 to a detector 62 which measures the intensity of the emitted light. A device such as a meter 64 is connected to detector 62 and supplies a read-out of the intensity of the emitted light detected in detector 62 to provide a fluorometric measurement of the intensity of the emitted light and, therefore, the fluorescence of the fluorescently excited substance in test sample 54.

Another frontal approach type of fluorometer which is suitable for measuring the fluorescence of samples in wells 26, 26a is described in application Ser. No. 433,825, filed Oct. 12, 1982, now U.S. Pat. No. 4,501,970, issued Feb. 26, 1985. This related application is assigned to the assignee of the subject application.

From the foregoing description it will be appreciated that the beam of exciting light 42 enters through the open upper end of the sample-holding vessel, and that the light emission due to the fluorescent excitation of sample 54 exits through the open upper end of the vessel. The provision of barrier 34 in the form shown in FIG. 1 or in the form shown in FIG. 3 therefore does not interfere with the entrance of exciting light or the exit of emitted light.

It is evident from the foregoing that any suitable frontal approach type of fluorometer may be used with sample-holding vessels containing the barrier of this invention. The particular type of frontal approach fluorometer therefore does not constitute a part of this invention.

Figure 5:
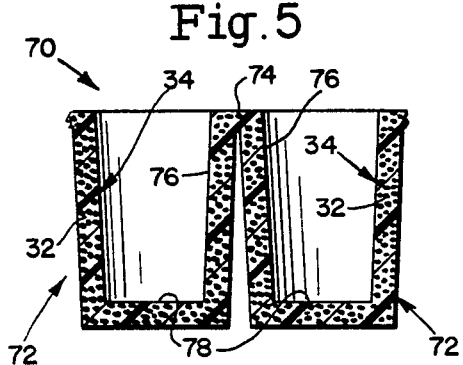
FIG. 5 is an enlarged fragmentary section taken substantially along lines 5—5 of FIG. 4.

In FIGS. 4 and 5, the pigment-defining barrier of this invention is shown to be incorporated into a molded, one-piece microtest strip 70 containing a straight row of parallel, upwardly opening wells 72 for containing microliter quantities of liquid. In this embodiment, each of the wells 72 is formed with a cylindrical side wall 76 and a flat bottom wall 78 as shown in FIG. 5.

Each of the wells 70 is integrally joined to the adjacently disposed wells by frangible stem-like segments 74 which may take the form of mold flashings. Segments 74 lie flush with the lips or open upper ends of wells 72. Segments 74 are easily broken by hand to enable one or more of the wells 72 to be separated from the strip. One of the disconnected wells 72 is shown in FIG. 7.

Wells 72 are provided with precise, uniform dimensions. The longitudinal axes of wells are parallel and contained in a common plane.

The previously mentioned Thorne patent discloses a matrix of wells which are integrally joined together by frangible stems for separation into individual wells and also into strips of the type shown in FIG. 4. It will be appreciated that the principles of this invention may be applied to the well structure described in the Thorne patent. The disclosure of the Thorne patent is hereby incorporated into this specification by reference.

Strip 70 is preferably formed from polystyrene or polyvinyl chloride. Alternatively, strip 70 may be formed from any of the other moldable materials mentioned for plates 20 and 20a.

Where strip 70 is formed from polyvinyl chloride, the individual wells 72 may be integrally joined together by a thin severable segment portion (not shown) which can easily be cut with scissors.

A holder of the type shown and described in the Thorne patent may be used to support strip 70 and/or the individual wells. Alternatively, any other suitable holder may be used to support the strip while conducting an assay. If desired the holder itself may be provided with the barrier of this invention.

Like the embodiment shown in FIG. 2, pigment particles 32 are uniformly distributed or dispersed throughout strip 70 in sufficient quantity or density to form the required barrier 34 which blocks any significant penetration of the fluorometer's exciting light or radiation into strip 70, thereby preventing any significant excitation of the strip's plastic material during a fluorometric measurement. The pigment-defining barrier for strip 70 therefore has the effect of supressing the native fluorescence of the strip's plastic material in the same manner described for the embodiment of FIG. 2.

The pigments used to form the barrier in the embodiment of FIG. 2 are intended for use to form the barrier in strip 70. Like FIG. 2, black or white pigment is especially suitable for forming the barrier in strip 70. The amount of pigment used to form the barrier in strip 70 is the same as that described for the embodiment in FIG. 2.

In manufacturing strip 70, it is evident that pigment particles 32 are first thoroughly mixed with the plastic material prior to molding strip 70. Thereafter, strip 70 is molded from the mixture of the plastic material and pigment particles so that the pigment particles are captured or suspended in the solidified, molded plastic body to define the barrier 34.

Figure 6:
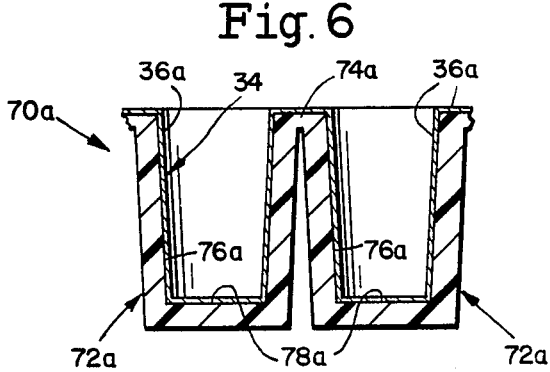
FIG. 6 is an enlarged fragmentary section similar to FIG. 5, but illustrating the coated barrier embodiment.

Instead of dispersing the barrier-defining pigment particles 32 into the strip's plastic body, the barrier 34 may be established by applying a thin coating or layer of pigment 36a to the exposed surfaces of a preformed microtest strip 70a and especially to those surface areas which will be exposed to the fluorometer's exciting light as shown in FIG. 6. Strip 70a has the same configuration as strip 70 and is of the same construction as strip 70 except that the coating 36a is applied in lieu of dispersing the pigment particles throughout the strip's plastic body. The body of strip 70a is therefore devoid of pigment and is formed entirely of a suitable moldable material such as polystyrene or polyvinyl chloride. To the extent that strips 70 and 70a are the same, like reference numerals have been applied to designate like parts, except that the reference numerals used for strip 70a have been suffixed by the letter "a" to distinguish them from those used for strip 70.

Coating 36a is the same as coating 36 and may be formed from those pigments used for coating 36, such as white or black. Coating 36a is applied to the interior surfaces of well 72a. It may optionally be applied to the upwardly facing surface of strip 70a as shown. Covering the upwardly facing surface of strip 70a with coating 36a, however, is not necessary.

In place of the pigment coatings 36 and 36a, a layer of silver or other suitable metal (not shown) may be deposited on the surfaces covered by pigment coatings 36 and 36a. The metal layer is required to be opaque at least to the wave lengths of the fluorometer's emitted light. In addition, the metal deposit is required to be non-fluorescent or at least exhibit a low fluorescence (significantly less that that of the material used to mold the sample-receiving vessels) at the wave length or wave length range of the light which is emitted by fluorescently exciting the test samples or other substances placed in the sample-receiving wells.

In addition to the microtest plates and microtest strips, the barrier of this invention may be incorporated into any other sample-holding vessel, such as a cuvette or a test tube. The vessels incorporating the barrier of this invention are preferably molded. Any suitable conventional molding technique may be utilized, such as injection molding, thermoforming and casting. Injection molding is commonly used for manufacturing polystyrene microtest plates, strips and other vessels. For manufacturing polyvinyl chloride microtest plates, strips and other vessels, the barrier-defining pigment is first mixed thoroughly with the plastic resin, and the mixture is then extruded into a sheet. Thereafter, the sheet is thermoformed into the microtest plates, strips and other vessels.

From the foregoing description, it is clear that the microtest plates, strips and other vessels incorporating the barrier of this invention, may be placed directly in a fluorometer of the type shown in FIG. 7 for measuring the fluorescence of a test sample in wells 26, 26a, 72, and 72a. Where microtest plates 20 or 20a are inserted into the fluorometer, it is understood that either the plate or the fluorometer's exciting light beam must be shifted to separately measure the fluorescence of each sample. Any conventional carrier (not shown) may be used for shifting the microtest plate in an X-Y plane to target each well separately. The same applies where the microtest strip or a portion of the microtest strip is inserted into the fluorometer.

In conducting a fluorescent immunoassay with the microtest plates or microtest strips described above, it is evident that the test samples are first prepared in the sample-receiving wells. Thereafter, the entire microtest plate, the entire microtest strip or, the individual wells (as in the case of the microtest strip) is placed in the fluorometer for conducting the fluorometric measurement of the test sample. The measurement of the test sample's fluorescence is then used to determine the quantity of the substance of interest in the test sample as outlined in the introductory portion of this specification.

Figure 8:
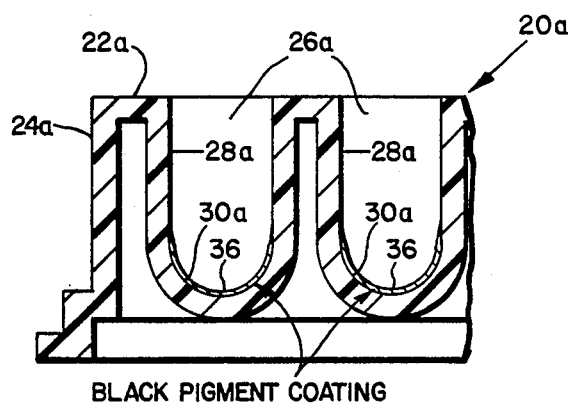
FIG. 8 is an enlarged fragmentary section similar to FIG. 3, but illustrating a modification of the barrier-defining coating.
Figure 9:
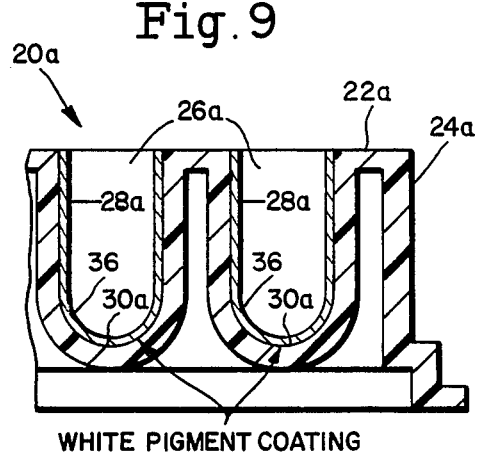
FIG. 9 is an enlarged fragmentary section similar to FIG. 3, but illustrating another modification of the barrier-defining coating.
Figure 10:
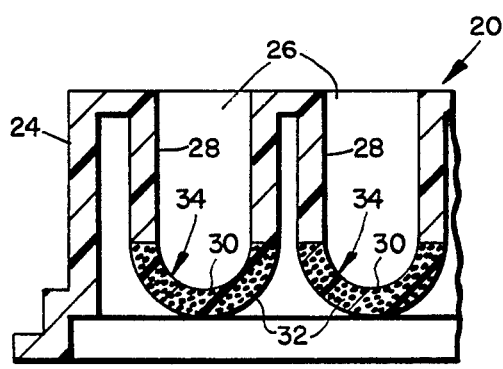
FIG. 10 is an enlarged fragmentary section similar to FIG. 2, but illustrating a modification in which black pigment particles are dispersed in separately formed bottom walls for the microtest plate.

In using a fluorometer of the frontal approach type to conduct the fluorometric measurement, it is not essential that the top wall 22a of the microtest plate 20a be covered by coating 36. Instead, for a black-pigmented coating, only interior surfaces of the bottom walls 30a of the sample-holding wells 26a are required to be covered with coating 36 as shown in FIG. 8 because the black pigment absorbs all light wave lengths and reflects none. For a white-pigmented coating, however, the interior surfaces of the side walls 28a of the wells 26a as well as the interior surfaces of the wells' bottom walls 30a must be covered with coating 36 as shown in FIG. 10 because the white pigment will reflect the fluorometer's exciting light and the light emitted by the fluorescently excited test samples.

In view of the foregoing teaching it also will be appreciated that plate 20 could be manufactured in such a way that the pigment particles 32 are dispersed only in those regions to be exposed to the fluorometer's exciting light and any reflections thereof. For example, the bottom walls 30 of wells 26 could be molded separately of the remainder of plate 20 and thereafter bonded or otherwise suitably joined to the side walls 28 of wells 26 as shown in FIG. 10. For such an embodiment, the barrier-defining pigment particles 32 will be dispersed throughout the separately formed bottom walls 30, but not in the remainder of plate 20 so that barrier 34 will be formed in the bottom walls 30, but not in the remainder of plate 20. For this embodiment, the barrier-defining pigment particles 32 are required to be black so that the black-pigmented bottom walls 30 will absorb all wave lengths of the fluorometer's exciting light which is directed downwardly through the open ends of the wells in the manner shown in FIG. 7.

Figure 11:
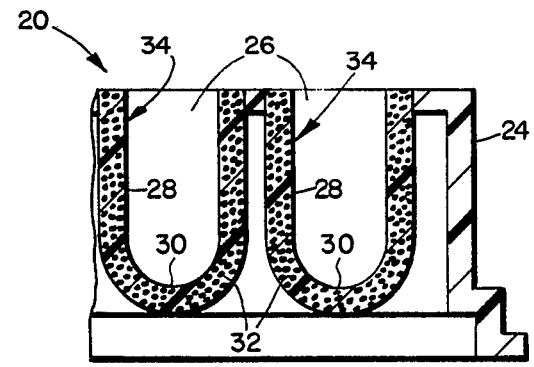
FIG. 11 is an enlarged fragmentary section similar to FIG. 3, but illustrating another modification in which white pigment particles are dispersed in separately formed wells for the microtest plate.

Alternatively, where it is desired to use white pigment, rather than black, the wells 26 in their entireties (including their side and bottom walls 28, 30) may be molded separately from the remainder of plate 20 and thereafter suitably joined to the plate's top wall 22 as shown in FIG. 11. For such an embodiment, the white pigment particles will be dispersed throughout the separately formed wells to form barrier 34, but will not be present in the remainder of plate 20. Accordingly, the white-pigmented barrier 34 will be present in the side and bottom walls of wells 26, but not in the remainder of plate 20.

Regarding strip 70a, it will be appreciated that where the black pigment coating is used, only the interior surfaces of the wells' bottom walls 78a are required to be coated because the fluorometer's exciting light enters through the open upper end of each well and only impinges on the bottom wall of each well. The exciting light will therefore be absorbed by the black pigment coating (36a) on each bottom wall 78a and consequently will not be reflected, thereby obviating the need for coating the side walls of wells 72a.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method comprising: making a microtest well structure for use in a system for conducting frontal approach assays of immunological substances wherein a labeled reactant is immunologically reacted with an immunological substance which is directly or indirectly immobilized on a solid phase to yield a light emitting reaction product wherein the energy release of said reaction product is measured to determined the quantity of the substance by,
   providing a plastic material having a native fluorescence and sufficient protein-binding properties to serve as the solid phase in said assay;
   providing a pigment barrier means being substantially opaque and substantially non-fluorescent for enhancing the signal-to-noise ratio of said well structure; and
   molding from said plastic material a plurality of interconnected, open-top wells for receiving microliter quantities of fluid samples during a measurement, each of said wells having an interior surface consisting of cylindrical side walls and a bottom and embedding said pigment barrier means at least in the interior surface of said wells surrounding the sides and bottom of said wells in a concentration of at least 0.01 percent, by weight, of said structure.

2. The method defined in claim 1 wherein said structure is a microtest plate having a plurality of sample holding cavities in the form of uniformly spaced apart wells arranged in a plurality of parallel spaced apart rows.

3. The method defined in claim 1 wherein said structure is a microtest strip having a plurality of sample holding cavities in the form of open top wells arranged in a straight row.

4. The method defined in claim 1 wherein said barrier means is a particulate black pigment.

5. The method defined in claim 1 wherein said barrier means is a particulate white pigment.

* * * * *